United States Patent [19]
Marshall et al.

[11] Patent Number: 6,149,608
[45] Date of Patent: Nov. 21, 2000

[54] SKIN PRICKERS

[75] Inventors: Jeremy Marshall, Oxford; Glenn Davison, Oxfordshire; Adam John Mumford, Oxford, all of United Kingdom

[73] Assignee: Owen Mumford Limited, Oxford, United Kingdom

[21] Appl. No.: 09/242,716

[22] PCT Filed: Jun. 19, 1998

[86] PCT No.: PCT/GB98/01636

§ 371 Date: Feb. 22, 1999

§ 102(e) Date: Feb. 22, 1999

[87] PCT Pub. No.: WO98/58584

PCT Pub. Date: Dec. 30, 1998

[30] Foreign Application Priority Data

Jun. 21, 1997 [GB] United Kingdom .................... 9713077

[51] Int. Cl.[7] ........................................................ A61B 5/00
[52] U.S. Cl. .......................... 600/573; 600/583; 604/110; 606/181
[58] Field of Search ............................. 600/583; 604/110; 606/181, 182, 192, 198

[56] References Cited

U.S. PATENT DOCUMENTS

| 5,423,847 | 6/1995 | Strong et al. | 606/181 |
| 5,558,651 | 9/1996 | Crawford et al. | 604/110 |
| 5,702,369 | 12/1997 | Mercereau | 604/110 |

*Primary Examiner*—Cary O'Connor
*Assistant Examiner*—Pamela Wingood
*Attorney, Agent, or Firm*—Young & Thompson

[57] ABSTRACT

After removal of a protective cap, the forward end of a barrel (1) of a skin pricker is placed against the skin and the user presses the projecting end of a trigger (6) forwards. As the trigger pivots about a fulcrum (9) of the barrel (1), a thin bridge onto a lancet (2) shears. The lancet is released, and shoots forward as a spring (3) extends, thus projecting a needle tip (4) to prick the skin. This projection is only momentary and the lancet (2), which is captive to the spring (3), is pulled back as the spring (3) reverts to a recovery position where the needle tip is safe inside the barrel. The trigger (6), although broken away from the lancet, remains captive to the barrel by the enlargement (11). The lancet cannot again be operated to eject the needle and the pricker is then intended to be discarded.

17 Claims, 3 Drawing Sheets

SKIN PRICKERS

CROSS REFERENCE TO RELATED APPLICATION

This application is the 35 USC 371 National Stage of International application PCT/GB98/01636 filed on Jun. 19, 1998, which designated the United States of America.

FIELD OF THE INVENTION

This invention relates to skin prickers for drawing small drops of blood for analysis. These have been developed so that they are cheap enough not only for the lancet whose tip penetrates skin to be thrown away after a single use, but also for the whole device which contains and fires the lancet to be discarded. Such wastage is justifiable in that it eliminates the risk of infection, sometimes fatal, from used lancets.

BACKGROUND OF THE INVENTION

These throw-away devices automatically retract the lancet after the tip has momentarily projected, and they are designed so that it is virtually impossible to get at the lancet after such use. However, such an objective is not always achieved, and by using a tool, for example, it is sometimes possible to reset the lancet.

Another problem facing the designer of such a device is to make it as simple as possible, with the minimum number of parts to manufacture and assemble. If the device is to be thrown away after a single use, anything too complex is costly and unacceptable.

OBJECT OF THE INVENTION

It is the aim of this invention to provide a skin pricker which is a "throwaway" after a single use, which is of very simple construction, and which, short of destruction, does make it virtually impossible to have access to the lancet after use.

In our International Patent Application No. PCT/GB98/01237 we have proposed a skin pricking device which should fulfil these requirements. It comprises a barrel containing a spring loaded lancet releasable from a primed rearward position momentarily to project its tip from the forward end of the barrel and then retract it, wherein the priming and release means for the lancet are combined in an element projecting laterally from the lancet through a longitudinal slot in the barrel, the element having a weakness enabling it to be broken off having been shifted to a catch formation retaining it at the rear end of the slot, the breaking off releasing the lancet.

We now have a further proposal, making the device even simpler to use by eliminating the priming step.

SUMMARY OF THE INVENTION

According to the present invention there is provided a skin pricker comprising a lancet spring loaded in such a manner as to be releasable from a primed rearward position so as momentarily to project its tip from the forward end of the barrel and then retract it, wherein the lancet is formed integrally with a trigger that projects outwardly through an aperture in the forward end of the barrel, there being a shearable bridge within the barrel between the trigger and the lancet, and wherein, in manufacture, the barrel is closed around the lancet to form the aperture and capture the trigger, which keeps the spring means primed, the actuation of the trigger shearing the bridge and releasing the lancet.

Preferably, the aperture and trigger are so formed that, after shearing away from the lancet, the trigger remains captive to the barrel.

Conveniently, the trigger is designed to be actuated so as to pivot its externally projecting end towards the forward end of the barrel. The wall of the aperture on which the trigger bears provides a fulcrum and the leverage that is thereby achieved makes shearing of the bridge (which will be very close to the fulcrum) quite easy.

Preferably, the lancet tip is shielded by a cap which has an exposed end forward of the barrel. When the user is ready, this can be twisted off, shearing a narrow neck at the root of the needle tip. The cap maintains the sterility of the needle before use and it provides a guard should the trigger be accidentally sheared off and the lancet fired.

Conveniently, the barrel is made in two generally semi-cylindrical halves, which may be integrally moulded, and which are folded together to join in a diametral plane.

Advantageously the barrel may incorporate at least one internal longitudinal channel in which projecting portions on the lancet can slide, but which prevents rotational movement of the lancet.

BRIEF DESCRIPTION OF THE DRAWINGS

For a better understanding of the invention, one embodiment will now be described, by way of example, with reference to the accompanying drawings, in which.

DETAILED DESCRIPTION OF THE INVENTION

Figure 1:
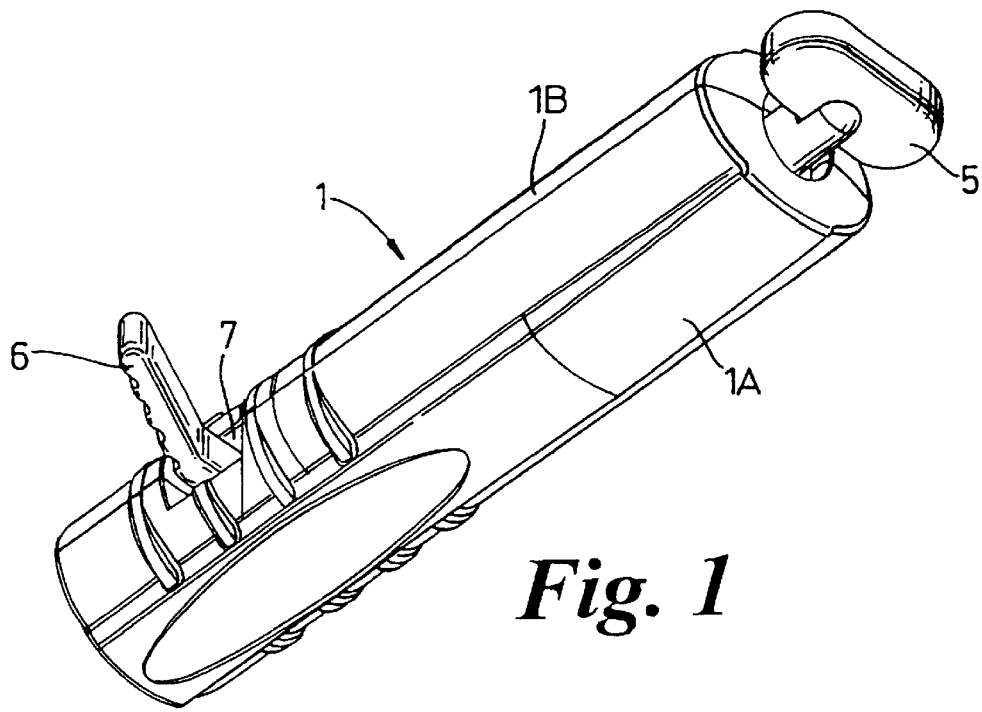
FIG. 1 is a perspective view of a skin pricker of this invention before use.

The pricker of FIGS. 1 to 4 has a two part barrel 1, the two parts 1A, 1B being generally semi-cylindrical. It houses a lancet 2 and a coil spring 3, the needle tip 4 of the lancet being initially shielded by an elongate cap 5 that projects through an aperture 12 at the forward end of the barrel 1.

The plastics body of the lancet 2 has a trigger 6 integrally moulded at its rear end. This trigger extends generally radially through an aperture 7 formed when two cut-outs formed in the parts 1A, 1B of the barrel come together. The trigger is joined to the lancet body by a thin bridge 8. The forward side of the body of the barrel forming the aperture 7 provides a fulcrum 9 about which the trigger can be pivoted. The trigger has a waist 10, whilst the inner end 11 of the trigger is enlarged and incapable of passing through the aperture 7.

Figure 2:
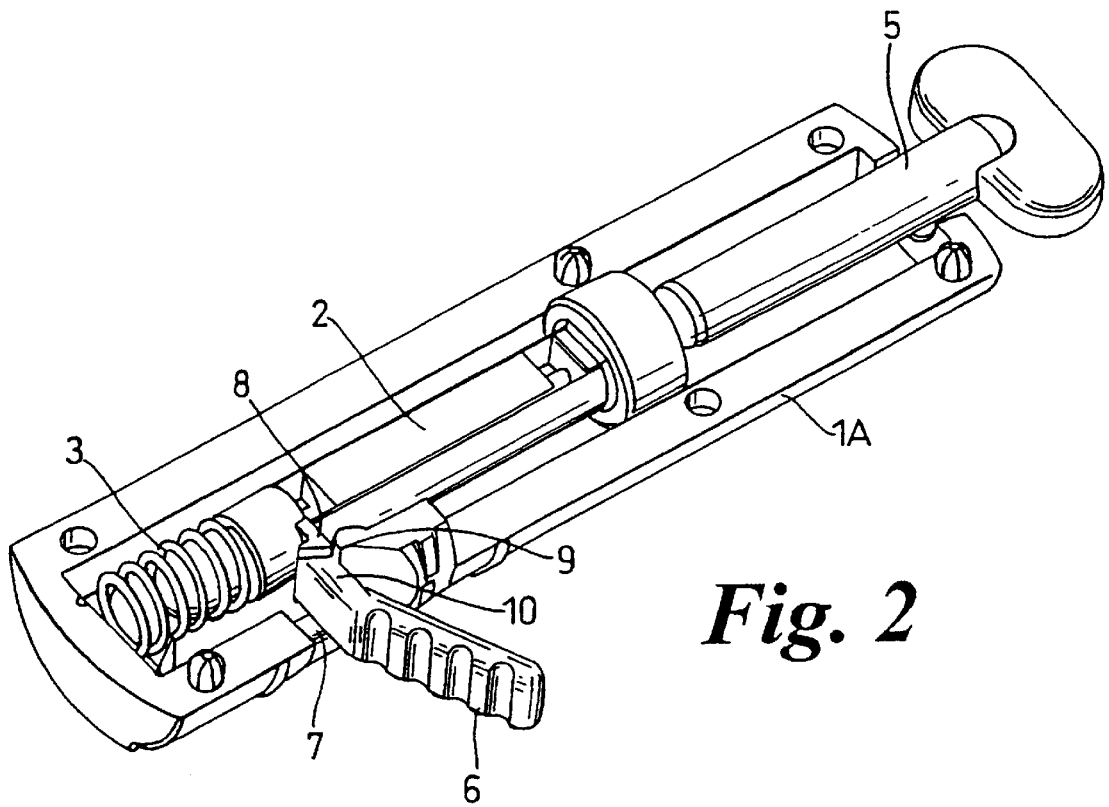
FIG. 2 is a perspective view of the pricker of FIG. 1 before use with half its barrel removed.
Figure 3:
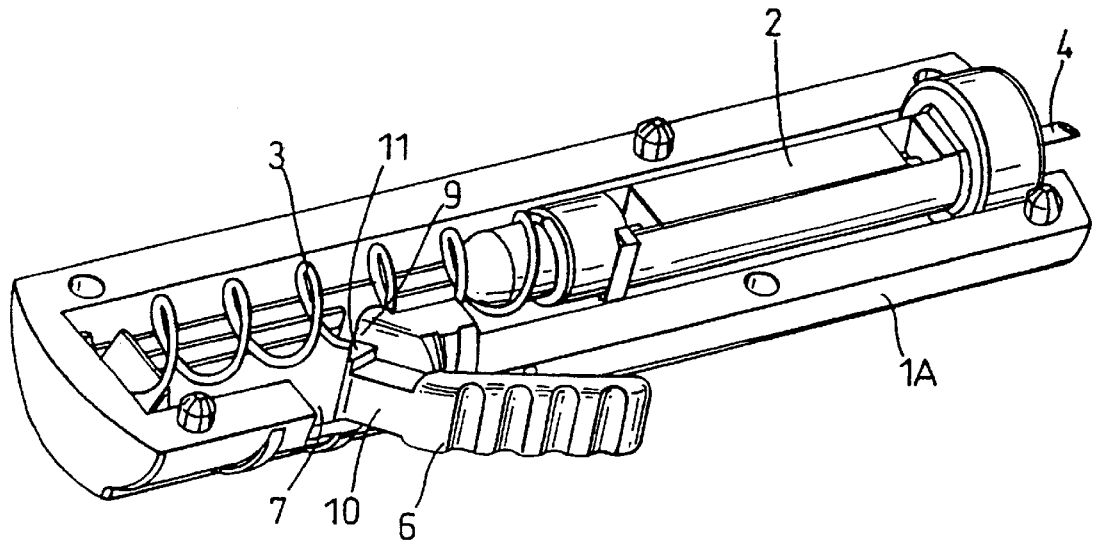
FIG. 3 is a perspective view of the pricker as in FIG. 2 but at the point of use.
Figure 4:
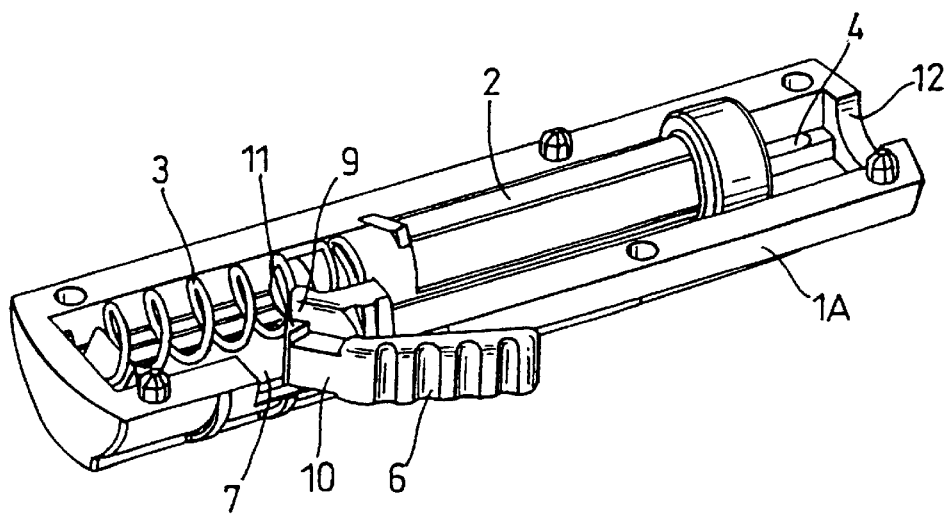
FIG. 4 is a perspective view of the pricker as in FIG. 2 but after use.

The pricker is assembled with its components as shown in FIG. 2, that is with the spring 3 compressed and the lancet 2 retracted.

For use, the cap 5 is twisted off in known manner. The lancet is held against rotation by virtue of the fact that the trigger 6 is captive in the aperture 7. The forward end of the barrel with the aperture 12 is placed against the skin and the user presses the projecting end of the trigger 6 forward. As the trigger pivots about the fulcrum 9 the thin bridge 10 shears. The lancet is released, and shoots forward to the FIG. 3 position as the spring 3 extends, thus projecting the needle tip into the skin. This projection is only momentary and the lancet 2, which is captive to the spring 3, is pulled back to the FIG. 4 position, as the spring reverts to a recovery position, where the needle tip is safe inside the barrel. The trigger 6, although broken away from the lancet, remains captive to the barrel by the enlargement 11.

Figure 5:
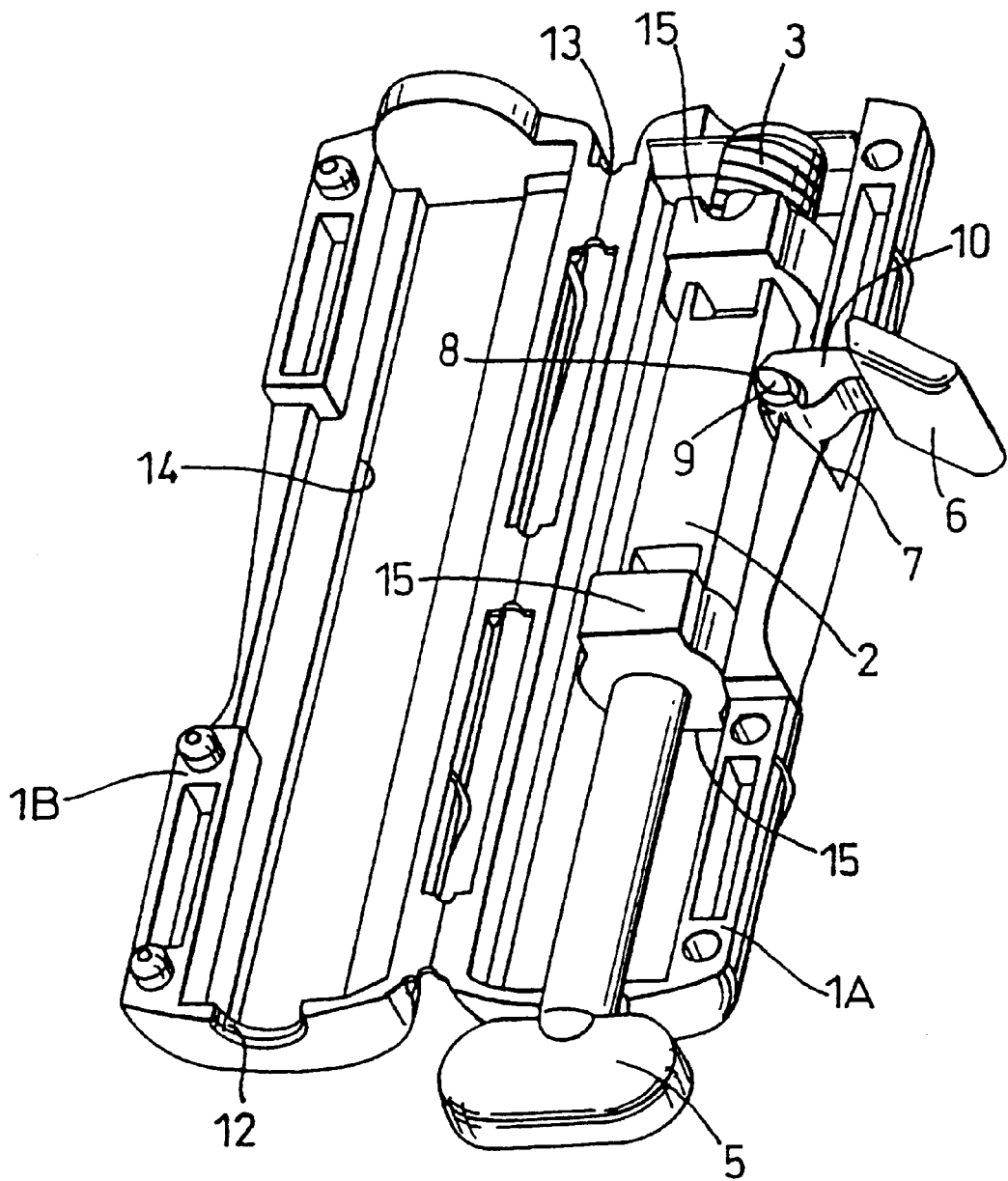
FIG. 5 is a perspective view of two parts of the barrel of an alternative form of skin pricker of this invention in an open state during assembly.

In the device shown in FIG. 5, similar parts to those of the embodiment of FIGS. 1 to 4 are given the same reference numbers. The two parts of the barrel 1A and 1B are integrally moulded to form a connecting hinge 13 and incorporate channels 14 within which projections 15 on the lancet 2 can slide. These ensure that the lancet does not rotate as the cap 5 is unscrewed which could result in premature firing of the needle if the thin bridge 8 was to be sheared. Once the pricker is assembled operation by pressing the projecting end of the trigger 6 towards the forward end of the barrel 1 is much the same as for the device of FIGS. 1 to 4.

What is claimed is:

1. A skin pricker comprising a lancet spring loaded in such a manner as to be releasable from a primed rearward position so as momentarily to project its tip from the forward end of a barrel and then retract it, wherein the lancet is formed integrally with a trigger that projects outwardly through an aperture in the forward end of the barrel, there being a shearable bridge within the barrel between the trigger and the lancet, and wherein, in manufacture, the barrel is closed around the lancet to form the aperture and capture the trigger, which keeps the spring means primed, the actuation of the trigger shearing the bridge and releasing the lancet.

2. A skin pricker according to claim 1, wherein the aperture and trigger are so formed that, after shearing away from the lancet, the trigger remains captive to the barrel.

3. A skin pricker according to claim 1, wherein the trigger is designed to be actuated so as to pivot its externally projecting end towards the forward end of the barrel.

4. A skin pricker according to claim 1 wherein the wall of the aperture on which the trigger bears provides a fulcrum and the leverage that is thereby achieved facilitates shearing of the bridge.

5. A skin pricker according to claim 1 wherein the lancet tip is shielded by a cap which has an exposed end forward of the barrel.

6. A skin pricker according to claim 1 wherein the barrel is made in two generally semi-cylindrical halves, which may be integrally moulded, and which are folded together to join in a diametral plane.

7. A skin pricker according to claim 1 wherein the barrel incorporates at least one internal longitudinal channel in which projecting portions on the lancet can slide, but which prevents rotational movement of the lancet.

8. A skin pricker according to claim 2, wherein the trigger is designed to be actuated so as to pivot its externally projecting end towards the forward end of the barrel.

9. A skin pricker according to claim 2, wherein the wall of the aperture on which the trigger bears provides a fulcrum and the leverage that is thereby achieved facilitates shearing of the bridge.

10. A skin pricker according to claim 3, wherein the wall of the aperture on which the trigger bears provides a fulcrum and the leverage that is thereby achieved facilitates shearing of the bridge.

11. A skin pricker according to claim 2, wherein the lancet tip is shielded by a cap which has an exposed end forward of the barrel.

12. A skin pricker according to claim 3, wherein the lancet tip is shielded by a cap which has an exposed end forward of the barrel.

13. A skin pricker according to claim 4, wherein the lancet tip is shielded by a cap which has an exposed end forward of the barrel.

14. A skin pricker according to claim 2, wherein the barrel is made in two generally semi-cylindrical halves, which may be integrally moulded, and which are folded together to join in a diametral plane.

15. A skin pricker according to claim 3, wherein the barrel is made in two generally semi-cylindrical halves, which may be integrally moulded, and which are folded together to join in a diametral plane.

16. A skin pricker according to claim 4, wherein the barrel is made in two generally semi-cylindrical halves, which may be integrally moulded, and which are folded together to join in a diametral plane.

17. A skin pricker according to claim 5, wherein the barrel is made in two generally semi-cylindrical halves, which may be integrally moulded, and which are folded together to join in a diametral plane.

* * * * *

UNITED STATES PATENT AND TRADEMARK OFFICE
CERTIFICATE OF CORRECTION

PATENT NO.   : 6,149,608
DATED        : November 21, 2000
INVENTOR(S)  : Jeremy Marshall et al.

It is certified that error appears in the above-identified patent and that said Letters Patent is hereby corrected as shown below:

<u>Column 3,</u>
Line 28, change "forward" to -- rearward --.

Signed and Sealed this

Tenth Day of September, 2002

*Attest:*

*Attesting Officer*

JAMES E. ROGAN
*Director of the United States Patent and Trademark Office*